United States Patent
Rantala

(10) Patent No.: US 8,120,434 B2
(45) Date of Patent: Feb. 21, 2012

(54) METHOD AND DEVICE FOR MEASURING IMPEDANCE

(75) Inventor: Arto Rantala, Espoo (FI)

(73) Assignee: Valtion Teknillinen Tutkimuskeskus, Espoo (FI)

( * ) Notice: Subject to any disclaimer, the term of this patent is extended or adjusted under 35 U.S.C. 154(b) by 154 days.

(21) Appl. No.: 12/495,267

(22) Filed: Jun. 30, 2009

(65) Prior Publication Data

US 2010/0001740 A1    Jan. 7, 2010

(30) Foreign Application Priority Data

Jul. 1, 2008   (FI) .................................. 20085682

(51) Int. Cl.
*H03K 3/03*    (2006.01)
*G01R 27/00*   (2006.01)

(52) U.S. Cl. ............ 331/57; 331/44; 324/600; 324/602; 324/605; 73/865

(58) Field of Classification Search ............ 331/44, 331/57, 116 R, 116 M, 154, 155; 324/600, 324/602, 605, 606, 615, 633, 652, 76.19, 324/76.39, 76.49, 76.51; 73/865
See application file for complete search history.

(56) References Cited

U.S. PATENT DOCUMENTS

| | | | |
|---|---|---|---|
| 3,906,340 A | | 9/1975 | Wingfield et al. |
| 5,895,629 A | * | 4/1999 | Russell et al. .................. 422/94 |
| 6,948,388 B1 | * | 9/2005 | Clayton et al. ............. 73/862.68 |
| 7,323,944 B2 | * | 1/2008 | Florescu et al. ................ 331/14 |
| 2001/0019271 A1 | | 9/2001 | Scott et al. |
| 2006/0001508 A1 | | 1/2006 | Ohara et al. |
| 2007/0001682 A1 | * | 1/2007 | Habitz et al. .................. 324/500 |
| 2007/0063617 A1 | | 3/2007 | Yamashita |

FOREIGN PATENT DOCUMENTS

| | | |
|---|---|---|
| EP | 1 679 512 A1 | 7/2006 |
| EP | 1 912 062 A1 | 4/2008 |
| WO | WO-2004/083839 A1 | 9/2004 |
| WO | WO-2007/030462 A2 | 3/2007 |

* cited by examiner

*Primary Examiner* — Ryan Johnson

(74) *Attorney, Agent, or Firm* — Birch, Stewart, Kolasch & Birch, LLP

(57) ABSTRACT

The invention relates to a method and system and microchip for determining impedance of a variable impedance component. The method comprises tuning a tunable oscillator over a predefined tuning range, the tunable oscillator having the variable impedance component coupled as a load thereof. The frequency response of the tunable oscillator is measured as a function of said tuning. Finally, the measured frequency response is analyzed for determining the impedance of the variable impedance component. The invention makes possible to manufacture smaller and simpler monolithic sensor microchips.

27 Claims, 4 Drawing Sheets

METHOD AND DEVICE FOR MEASURING IMPEDANCE

FIELD OF THE INVENTION

The invention relates to measurement of the change of impedance of a component as a function of frequency. Such measurements are required, for example, when reading sensors whose impedance is changed by the quantity sensed, such as mass.

BACKGROUND OF THE INVENTION

Measuring impedance as a function of frequency is generally used for obtaining data on the operation of various electrical components. One example of such component is a Film Bulk Acoustic Wave Resonator (FBAR) device which is based on the Bulk Acoustic Wave (BAW) technology. FBARs are easy to implement as monolithic structures, for example, on CMOS circuits. High resonance frequencies and quality factors are achievable using the FBAR technology. FBAR devices can be used, for example, as sensitive mass sensors because the impedance of the resonator changes as matter is positioned on a mass-loading area of the sensor. If an (bio) active layer is deposited on the mass-loading area of FBAR, one may achieve selectivity of substances to be measured and thus a selective (bio)sensor.

Traditionally, the impedance of FBAR sensors and the like is measured using laboratory-scale equipment, such as impedance analyzers or circuit analyzers, which measure the impedance of the component using very definite frequency excitation.

One solution for measuring the impedance of a resonator-type components or components that can be connected as part of a resonator, is to use so-called oscillator couplings. In the case of mass sensors, the purpose of such couplings is to determine the series or parallel resonance frequency of the oscillator as a function of mass change of the component. However, in practice it is often difficult or impossible to implement an operational and accurate oscillator coupling in particular as an integrated, ie. on-chip, structure. This is mainly because of the following reasons:

Resonators typically have inherently low coefficient of coupling or quality factor (Q-factor). A particular problem is related to measuring liquid-form samples, as the presence of liquid on a resonator drastically reduces the quality factor of the resonator.

Some components, such as FBAR sensors typically have several parallel resonance frequencies.

Resonators may have relatively large manufacturing tolerances, resulting in that their series/parallel resonance frequencies vary.

Large parasitism and parallel capacitance cause that the change of impedance as a function of frequency is relatively small. In addition, the phase will in practice never shift 180 degrees.

The above disadvantages apply in particular to FBAR sensors designed to be used as mass sensors, but may apply to other types of components too. Consequently, in practice oscillator couplings for impedance measurements can be taken advantage of only in the very limited case of high Q-factor resonators and absent or eliminated parallel resonances. In addition, very specific designs having low dynamic range must be used.

WO 2007/030462 discloses an interrogation circuit for inductive loads, comprising a voltage-controlled oscillator, a grid dip oscillator and phase locked loop. When signalled by the grid dip oscillator, the phase locked loop stops following the interrogation signal and remains producing a locked signal. The locked signal is passed to a frequency counter. Thus, by means of such circuit, measurements only at a point frequency can be carried out. In addition, the circuitry required by such a solution is relatively complex and not as such suitable for sensor devices having the interrogation circuit integrated therein as a single monolithic structure. The circuit is also expensive and as such not suitable to be used in connection with disposable sensor devices.

SUMMARY OF THE INVENTION

It is an aim of the invention to achieve a novel impedance measuring method which is accurate and can be implemented using simpler and thus also smaller electronics. It is also an aim to achieve a corresponding measurement system and a novel sensor device.

The aims of the invention are achieved by the method according to independent claims. In the method according to the invention the impedance of a variable impedance component is determined by tuning a tunable oscillator over a tuning range, the tunable oscillator having the variable impedance component coupled as a load thereof, measuring the frequency response of the tunable oscillator as a function of said tuning.

The impedance of the variable impedance component can be determined by analyzing the frequency response measured.

The steps of tuning and measuring are typically carried out at least twice in different loading states of the variable impedance component (e.g. a mass sensor unloaded and loaded with mass) and the step of analyzing comprises determining a difference in the respective resonating frequencies in at least one tuning point. This allows for determination of the impact of the load accurately.

The measurement system comprises a tunable oscillator, a variable impedance component coupled as a load of the tunable oscillator, means for tuning the tunable oscillator, and means for determining the frequency response of the tunable oscillator as a function of said tuning.

According to one embodiment, the variable impedance component is a resonator exhibiting at least two parallel resonance peaks. The measurement of impedance of such components has been difficult using conventional methods. However, by coupling the resonator as a load of an oscillator, the impedance can be accurately determined provided that the oscillator is tuned over the range covering the peaks. The method is described more closely later is this document.

In a particularly advantageous embodiment the frequency response of the oscillator is determined using a frequency counter or the like device which is connected directly to the oscillator. That is, there are no other oscillators or phase locking circuits in the system, which saves both space and costs, but provides for accurate detection of load changes of the oscillator.

A particular advantage of the invention is that it is suited not only for measuring certain types of resonators but for practically any kinds of components exhibiting change of impedance at given conditions.

In the case of resonators, the tuning range is selected to cover the resonance frequency (or frequencies) of the resonator and preferably also considerable ranges below and above that frequency (frequencies). According to one embodiment, a region in the vicinity of the resonance frequency (frequencies) is swept using smaller steps than regions farther from the resonance frequency. Regions farther from the resonance frequency (frequencies) can be utilized for determining a temperature compensation factor or other secondary parameters.

According to one embodiment, a sensor, such as mass sensor is used as the variable impedance component. According to a further embodiment, the sensor is of (bio)active type, ie. capable of selectively adhering desired (bio)molecules or (bio)particles on its surface or otherwise experiencing a mass change due to the presence of (bio)molecules or (bio)particles. As the present impedance analyser circuit design can be manufactured very small, even on chip with the sensor, the invention offers significant benefits in various (bio)sensing applications.

According to alternative embodiments, the sensor is a temperature sensor, pressure sensor, fluid flow sensor or acceleration sensor.

According to one embodiment, the variable impedance component is a resonator, such as a BAW resonator, in particular a FBAR. A microchip FBAR sensor device may comprise in a monolithic structure a tunable ring oscillator, an FBAR sensor coupled as the load of the tunable ring oscillator, and a terminal coupled to the tunable ring oscillator for measuring the oscillation frequency of the tunable ring oscillator. A monolithic frequency counter coupled to the terminal can be fabricated to the microchip too. The advantages of the present design in the challenging case of not only FBARs but also other resonators is discussed below in more detail.

The variable impedance component is preferably in direct ohmic, i.e. in essentially non-inductive and non-capacitive, contact with the oscillator.

An advantage of using the present invention in connection with small monolithic variable impedance components, such as semiconductor sensors, is that the total power consumption of the measurements can be kept very low compared with traditional laboratory-scale measurement techniques. Also the material and manufacturing cost can be kept very low, which makes it possible to manufacture even disposable sensor chips and the like.

According to one embodiment, the tunable oscillator is controlled using a digital control unit capable of sending digital control signal which is converted to an analogue control voltage using a D/A converter.

According to one embodiment, the tunable oscillator, and optionally also the digital control unit for the tunable oscillator and/or the D/A converter and/or the variable impedance component and/or counter for determining the oscillation frequency, are manufactured as a monolithic structure on a single semiconductor chip. Thus, a one-chip interrogation circuit for a sensor or even a fully functional the one-chip sensor device comprising both a sensor element and an interrogation circuit for the sensor can be manufactured.

According to one embodiment, the tunable oscillator is a voltage-controlled ring oscillator, for example comprising a set of series-coupled semiconductor inverters, such as CMOS inverters. This design is efficient, easy to manufacture and easy to integrate with other parts of the chip using techniques known per se.

If a resonator is used as the variable impedance component, its impedance change can be determined by determining, by controlling the tunable oscillator, an operation voltage at which the frequency response of the tunable oscillator is "locked" to a resonance frequency of the resonator, determining the change of response of the variable impedance component at or in the vicinity of said operation voltage between two different states of the variable impedance component (such as unloaded and mass-loaded state of a mass sensor).

The above measurement scheme provides a robust way of measuring the change of the impedance of the component, as well as some other parameters, at any or all of the several possible parallel resonance frequencies of the resonator. As is discussed and demonstrated in more detail below, reliable distinguishing of the parallel resonance frequencies and thus reliable measurements are achieved using the above measurement scheme. Implementation of the necessary steps can be automated in the system or done manually in part or in full.

The term "locking" is herein used to describe the tendency of the sensitivity of the oscillator to significantly change at a parallel resonance frequency of the resonator. In general, in the vicinity of the parallel resonance frequency, i.e. in the "locking region", the frequency of the oscillator still slowly changes with the control voltage, but the sensitivity of the df/dV is dramatically lower than in a non-locking region. Although important information is obtained from the measured response curves also at non-locking regions, as described later in more detail, determination the points where the derivative df/dV changes by jumps generally play a significant role when the measurement results are analysed.

According to one embodiment, the frequency response of the tunable oscillator is used for determining the impedance of the variable impedance component as a function of frequency, that is, at one or several frequency bands.

According to one embodiment, an array of oscillators, preferably manufactured on a single chip, each loaded or being capable of loaded with different variable impedance components, is used. Optionally, there may be one or more tunable oscillators loaded with a reference impedance for being able to carry out reference measurement, for example, for compensating environmental effects (eg. temperature variations) on the measurement.

According to one embodiment, the temperature compensation in the case of FBAR sensors is carried out by measuring the frequency response of the oscillator at least at two different points of operation and at least at two different temperatures and determining, using the at least two pairs of points obtained, a temperature compensation factor, such as the ratio of slopes of linearized temperature sensitivity responses. Then, this ratio can be used for intra- or extrapolating temperature compensation of measurement results obtained at a different point of operation.

The invention offers considerable advantages.

The accuracy of the impedance measurements is high. It is possible to determine impedance changes in particular for sensing applications very accurately.

The structure can be easily implemented and integrated using existing CMOS techniques The design allows for the manufacture of an array-type structure for measuring and/or comparing a plurality of impedances Due to the simplicity of the design, it is possible to determine the impedance using very high frequencies The effect of error sources, such as temperature variations, can be effectively minimized using reference measurements.

It should be noted that several methods and circuits are known in which sensors are controlled using an oscillator circuit. Such solution is disclosed, for example, in US 2006/001508. However, in such solutions, the tuning of the oscillator is not utilized in determining the impedance of the component in the same way as in the present invention.

The terms "component to be measured", "variable impedance component" or "DUT" are used to describe any component exhibiting a measurable impedance change when subjected to predefined conditions. Examples of suitable components are capacitors, inductors and resonators arranged to be sensitive to material properties of substance placed in their vicinity or into/onto their material-receptive portions. The material properties can be, for example, physical parameters such as mass or viscosity, electromagnetic parameters such as conductivity or permittivity. It is to be noted that measuring devices according to the invention can be manufactured independently of the components measured, whereby in some instances there may be provided one or more contact terminals for the component to be measured. On the other hand, in some embodiments both the component to be measured and the impedance-analyzing circuitry can be manufactured on the same semiconductor chip, for example.

Although it is the change in the electrical impedance of the component that causes the response of the present circuit to change, the change of the electrical impedance is in the case of sensors a result of a change in an internal property (eg. mass or temperature of a functional part of the component or distance between two functional parts of the component) of the component and/or the interaction of the component with its environment (eg. change of viscosity, pressure or electric/magnetic material properties in the vicinity of a functional part of the device). The term "impedance" in phrases like "determination of (change of) impedance" is to be understood widely to mean any measurable property or interaction of the component, the change of which shows as a change of the electrical impedance of the component. In other words, the basic idea of the invention can be applied to measuring the loading state of any component whose mechanical, electromechanical, electrical, electromagnetic or chemical loading shows in the oscillation frequency of the tunable oscillator coupled to the component. In addition, the term covers thus also such measurements where an absolute impedance value is not calculated, but the change of electrical impedance of the component is taken advantage of for determining some other property or interaction of the component. Even if not explicitly stated, the term "measurement/determination of impedance" is to be understood to cover also detection of impedance changes.

DETAILED DESCRIPTION OF EMBODIMENTS

Figure 1:
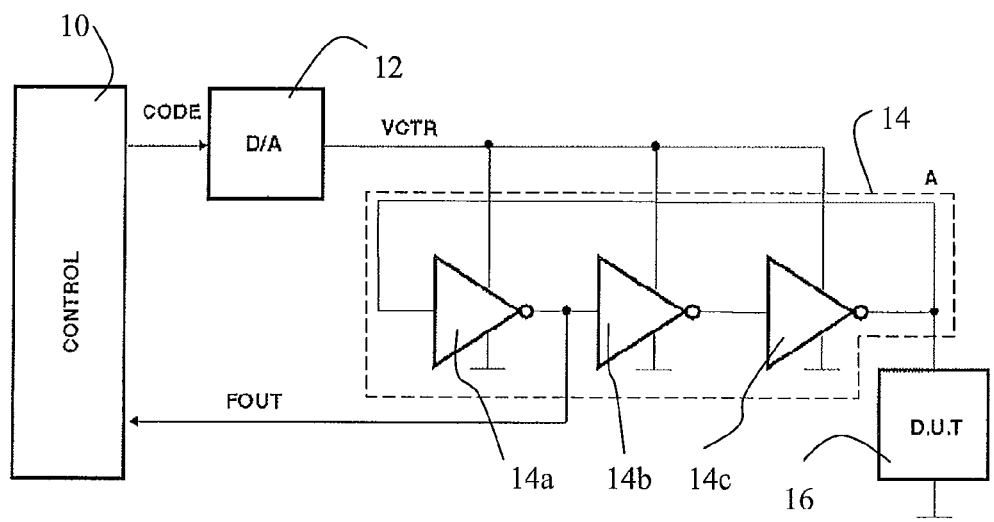
FIG. 1 shows a simplified circuit diagram of an impedance analyzer according to one embodiment.

Referring to FIG. 1, a control unit 10 capable of producing suitable digital control codes CODE is coupled to a digital-to-analogue (D/A) converter 12 for producing the analogue control voltage VCTR for an oscillator 14. The oscillator 14 comprises three CMOS inverters 14a, 14b, 14c which are coupled in series in an oscillating configuration. As the load of the oscillator there is connected a variable impedance component 16 (=DUT, device under test). The oscillation signal of the oscillator 14 is lead back to the control unit 10 for the output frequency FOUT being measured, for example, using a digital counter, and optionally being stored, visualized and/or further analysed.

The control unit 10 provides appropriate control signal for the oscillator, measures the output frequency of the oscillator, and, optionally further processes the results. The control unit 10 can be manufactured on the same wafer, such as a silicon wafer, as the oscillator portion, whereby monolithic implementation of functional analysis circuits is possible. The control unit 10 may comprise logic blocks/ports for a specific function only or the unit may be designed to be programmable in order to achieve a more generally usable device. A programmable control unit 10 ensures that the control of the oscillator and analysis of the results always corresponds to the impedance measured and quantities measured.

According to one embodiment, the tunable oscillator and the variable impedance component, and optionally also a digital control unit for the tunable oscillator are manufactured as a monolithic structure on a semiconductor chip.

In the method, the tunable oscillator 14 having the variable impedance component 16 as a load thereof, is controlled. The oscillator 14 is such that the change of impedance of the component 16, ie. the change of load as a function of frequency, affect the oscillation frequency of the oscillator 14. The tuning voltage, ie. the control voltage, can be generated using a buffered D/A converter. The frequency of the oscillator 14 is measured as a function of its tuning, ie the control voltage. As a result, one can determine parameters of the component 16 as a function of frequency. Measuring the frequency can be implemented using an externally clocked counter. The (change of) impedance can be determined by computing. The computing can be implemented using external computing means, for example, a separate computing circuit or computer, or using a computing unit integrated on-chip with the analyzer circuitry.

Figure 2:
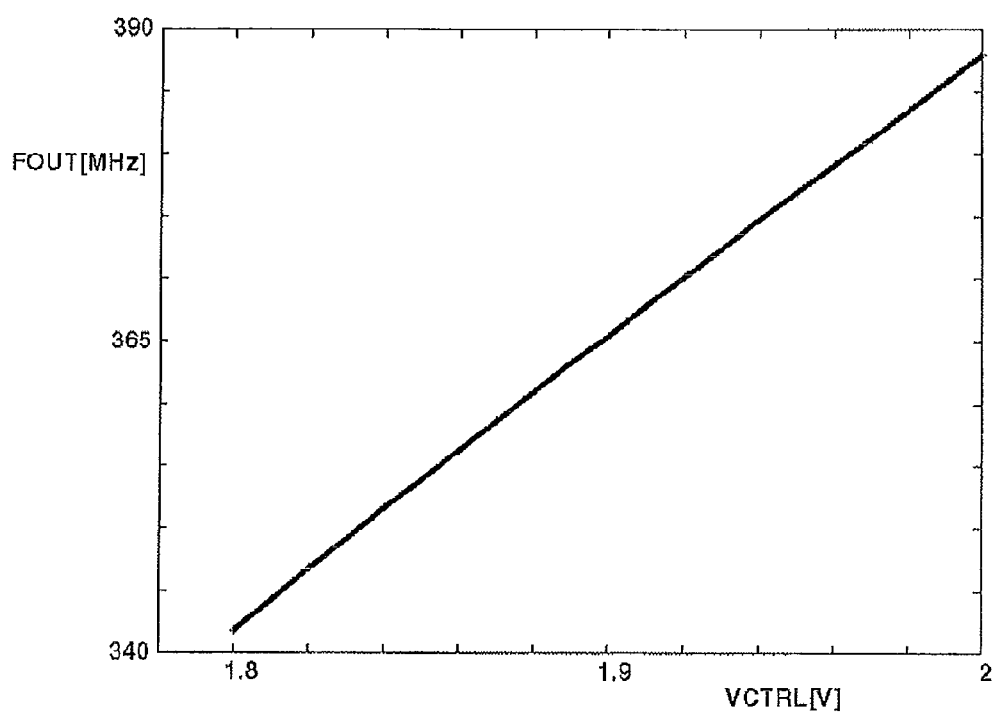
FIG. 2 depicts simulated output response (frequency) of the impedance analyzer according to FIG. 1 as a function of control voltage (voltage/frequency scales are by way of example only).

As is shown in FIG. 2, the output frequency vs. control voltage of an oscillator circuit according to FIG. 1 is roughly linear when unloaded. It has been found that also in a loaded condition, provided that the impedance-to-frequency of the component 16 is linear or at least monotonic, the response of the circuit stays linear at least at relatively narrow frequency bandwidths. On the other hand, if non-linear components 16 are measured the output frequency changes rapidly compared with the linear response of the inverter oscillator. Generally, it can be said that the rate of change of frequency as a function of control voltage is proportional to the absolute value of the rate of change of impedance of the component 16 measured. It is to be noted that the voltage/frequency values given in the figures are for illustrative purposes only and in reality can be chosen relatively freely by appropriate design and coupling of the components and the circuits.

The output of the measurement generally depends on the type of the load impedance and initial values of the measurement setup. For example, an FBAR gives a voltage-frequency graph different from that of a capacitor. However, for known types of load impedances, modelling/simulation of voltage-frequency graphs, and thus also the interpretation of measured the voltage-frequency graphs, is possible. The following description concentrates on the characteristics of resonator-type, in particular FBAR-type, load impedances.

Figure 3:
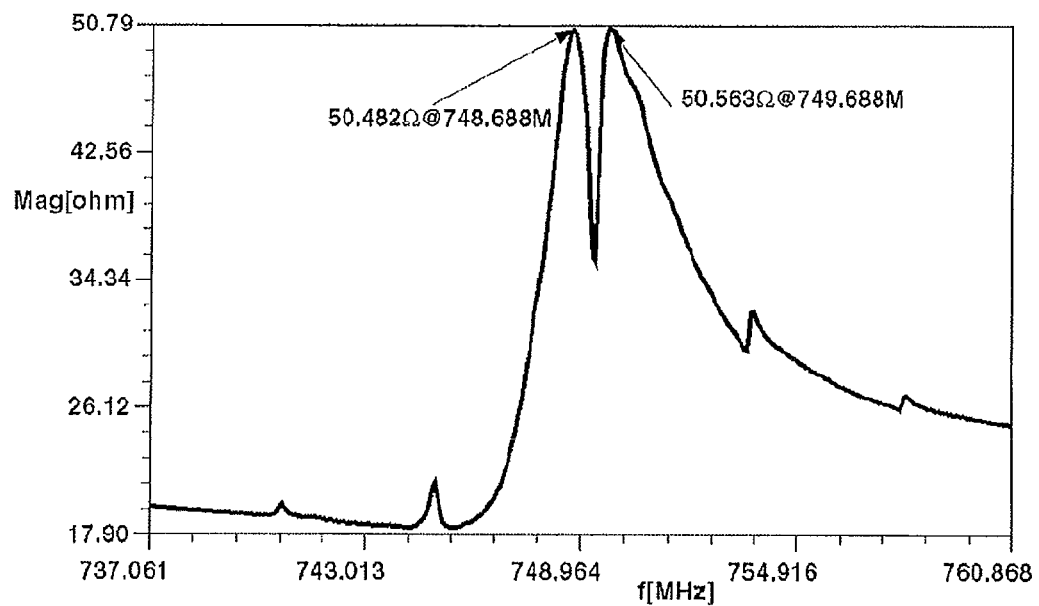
FIG. 3 shows the response of a FBAR as a function of excitation frequency measured using a circuit analyzer.

FIG. 3 shows a typical frequency response of an FBAR resonator measured using an ordinary circuit analyzer. The component is found to have two parallel resonance peaks at 748.688 MHz and 749.688 MHz. It is very challenging to design a traditional oscillator coupling for an FBAR like this because such an oscillator would lock to different output frequency depending on the initial parameters of the circuit or to switch frequency during operation ("leap" to another resonance peak). The parallel resonance peaks are, however, so close to each other that their filtering, for example using an LC-filter, is in practice not possible due to manufacturing tolerances. In addition, the parallel resonance frequency may vary tens of MHzs between different process runs, requiring the filter to be tunable.

The present impedance analysing circuit design is suitable also for FBARs having characteristics like shown in FIG. 3. In the following, the measurement and interpretation of the results are described by way of examples with reference to 4-7. The oscillator circuit used was basically according to FIG. 2 and manufactured as an IC-circuit using 0.35 μm AMS CMOS technology and wire bonded to a circuit board together with a bioactive FBAR. From the circuit board, the output frequency was measured as a function of control voltage.

Figure 4:
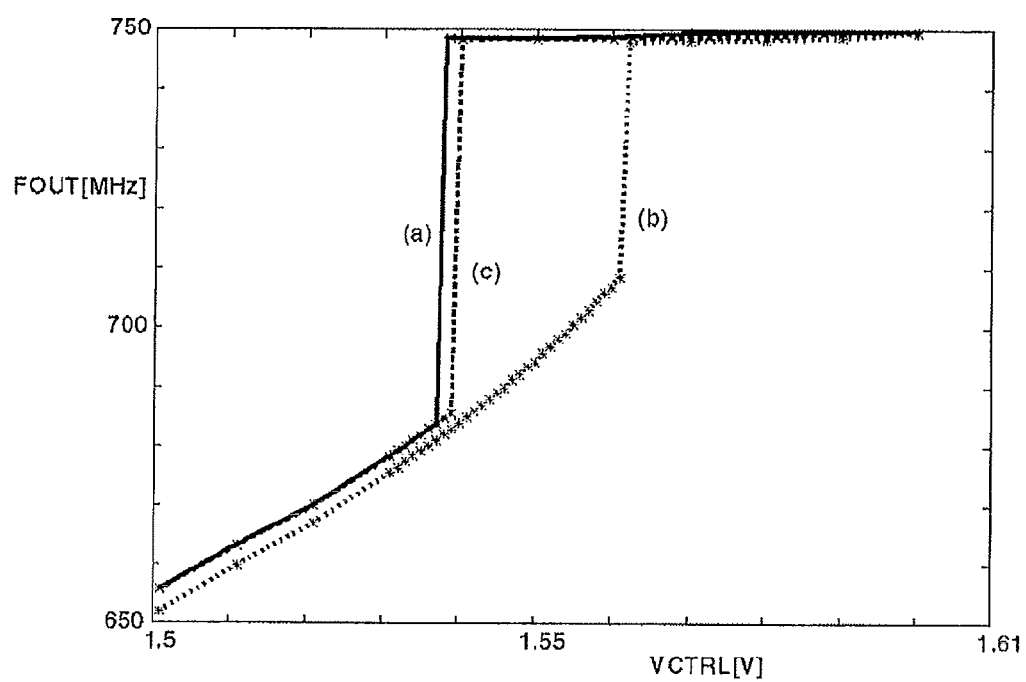
FIG. 4 illustrates the output response of a FBAR as a function of control voltage measured using the circuit according to FIG. 1, the FBAR (a) being in air at initial condition, (b) being immersed in water and (c) after having dried in air.

The wide-range frequency response of the circuit is shown FIG. 4 (FOUT vs. VCTR). It can be seen that the response is clearly different in all measured cases: FRAR in air in initial condition (a), FBAR immersed in water (b) and FBAR re-dried (c) in air.

From FIG. 4 one can deduct that the frequency increases by jump to the parallel resonance point of the component at a certain value of control voltage and when the output frequency exceeds the parallel resonance point of the resonator, the output voltage is locked. This voltage range, ie. range where the output frequency is being locked, is called the "point of operation" hereinafter. When the circuit locks into the vicinity parallel resonance peak, the output frequency of the oscillator is defined by the properties of the resonator, not the characteristic frequency of the oscillator.

When the locking frequency is used as the point of operation, one can determine, for example, the following parameters:
  Parallel resonance frequencies (see description of FIG. 5 below)
  Change of impedance as a function of given property (eg, change of mass)
  Environmental parameters of the resonator (eg. changes in temperature or viscosity, see description of FIG. 6 below).

Figure 5:
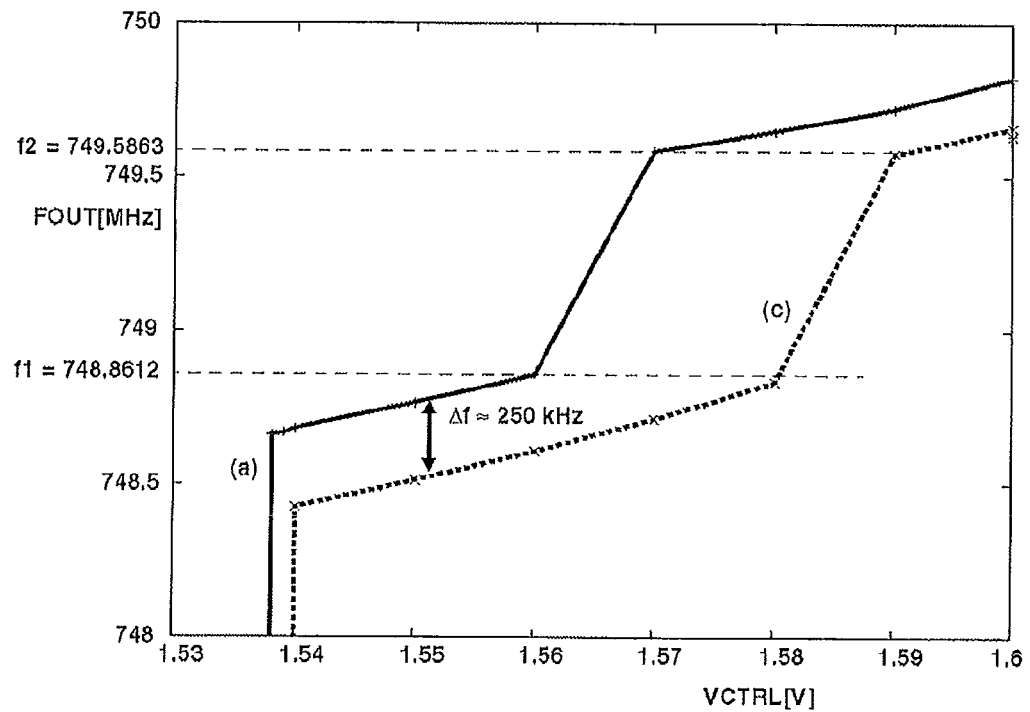
FIG. 5 shows a magnified portion of the graph of FIG. 4 (only data sets (a) and (c) shown).

FIG. 5 shows a picture of curves (a) and (c) zoomed at the point of operation. It can be seen, that after being immersed in water, the mass has increased because of contamination of the surface of the FBAR. This shows as the decrease of output frequency by $\Delta f$=250 kHz. In addition, it can be seen that as the control voltage is further increased, the slope of the curves is again rapidly increased. This is because of the second parallel resonance peak.

Figure 6:
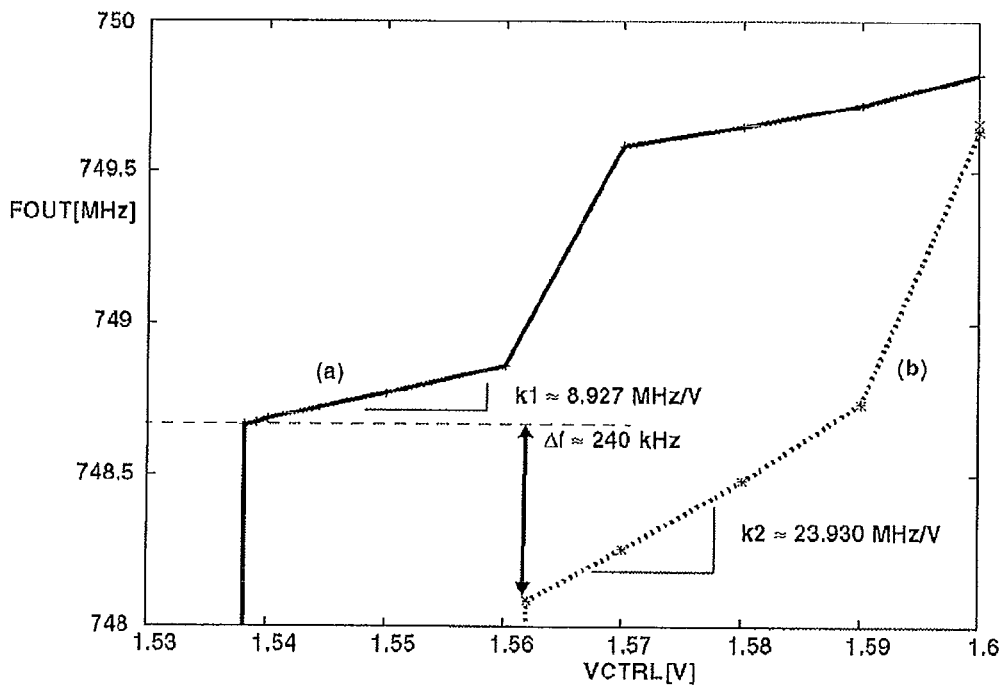
FIG. 6 shows a magnified portion of the graph of FIG. 4 (only data sets (a) and (b) shown).

FIG. 6 shows a corresponding magnified image of FIG. 4, now comprising curves (a) and (b). Again, one can see the contamination of the surface of the FBAR as a decrease of the output frequency by $\Delta f$=240 kHz. In addition the slopes of the curves at the point of operation are significantly different. This is because of the change of viscosity of the surroundings of the FBAR and thus different kind of resonation.

Figure 7:
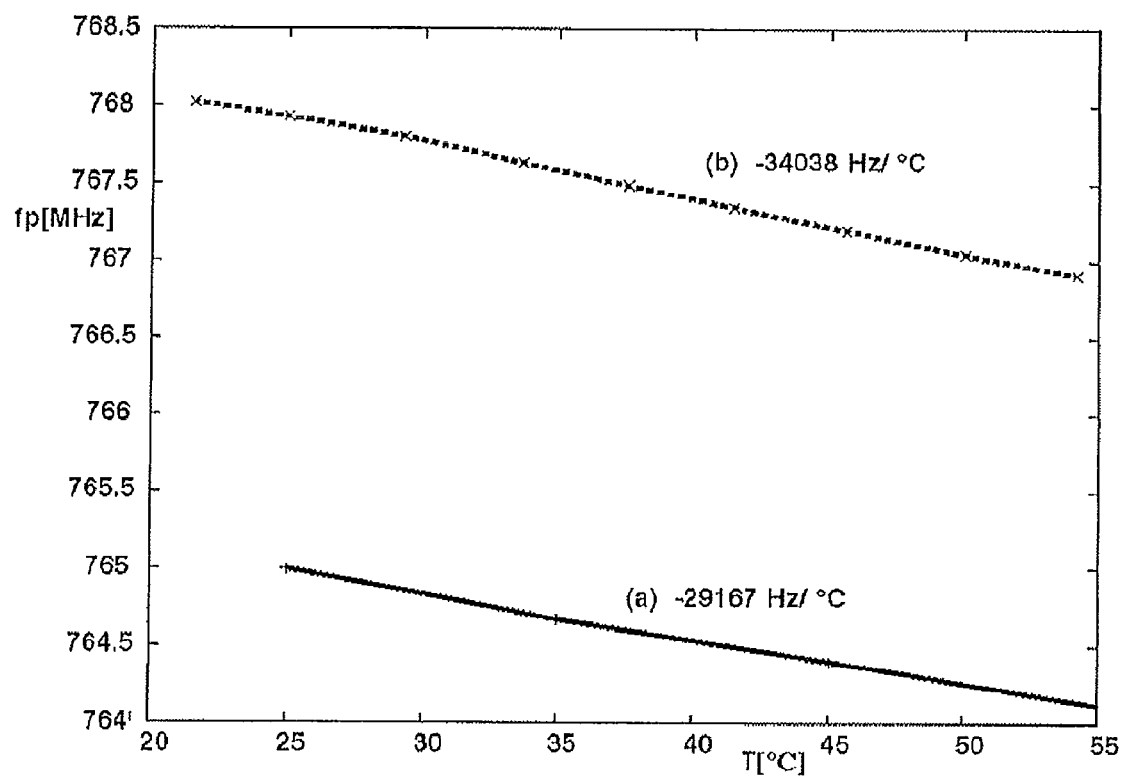
FIG. 7 depicts the measured temperature dependency of the parallel resonance peak of a two different FBARs using (a) circuit analyzer and (b) the present impedance analyzer.

FIG. 7 illustrates results of an experiment designed to characterize the temperature dependency of the present circuit design. FBAR components were measured before and after encapsulation at several temperatures. The change of parallel resonance frequency as a function of temperature using a conventional circuit analyser (a) and the present impedance analyser circuit (b). It must be noted that the measured FBAR components were situated on the same semiconductor wafer next to each other, whereby the manufacturing parameters of the components were maximally similar. From the results, one can see that the temperature dependency of the components is almost the same using both the measurement techniques, both the absolute values and the slopes being within process tolerances of the components.

When determining the impedance or environmental parameters, several values may be given for the control voltage and the measurement results can be averaged over a plurality of measurements made at these voltages in order to increase the precision of the measurement.

There are at least two main approaches for implementing a temperature compensation individually for each sensor device. According to first approach, there is provided a reference sensor, which is not sensitive to the quantity of interest of the actual sensor, that is, for example mass. The reference sensor may, for example, be coated in a different way such that no adhesion of matter to or erosion of matter from the surface takes place, like in the actual sensor. However, the reference sensor lying close to the actual sensor, typically on the same monolithic chip, the temperature of the sensors would be the same. Thus, the effect of temperature from the results can be compensated.

However, the temperature dependency of in particular FBAR resonators may vary significantly even if manufactured on a single chip. Therefore, another approach may be used in connection with such resonators. It has namely been observed that the temperature dependency of the response of the circuit having an FBAR sensor is different in different points of operation. With reference to FIG. 4, the response, including the temperature response, of the circuit at a low voltage level (i.e. <before "locking") is dominated by the response of the CMOS ring oscillator. However, when the circuit is "locked" at the parallel resonance, the response is dominated by the response of the FBAR (as can be seen from FIG. 7). Thus, a solution is to measure the frequency response of the oscillator at least at two different points of operation (the ring oscillator-dominated point and the FBAR-dominated point) and at least at two different temperatures and determining, using the at least two pairs of points obtained, the ratio of slopes of linearized temperature sensitivity responses. Then, this ratio can be used for intra- or extrapolating temperature compensation of measurement results obtained at a different point of operation. This is possible even if absolute temperature values were not known. This another approach does not require the fabrication of a separate reference sensor on the chip, but can be implemented by programming a suitable control algorithm for the circuit.

According to one embodiment, there is provided, on a single integrated chip, a plurality of oscillator circuits loaded with different components of interest. The plurality of oscillators are preferably controlled through a single control circuitry and D/A converter. By that way the difference of impedances of the components can be very accurately determined from the measured frequency responses.

According to one embodiment, there is provided a plurality of components to be measured, all having individual oscillator circuits connected to them, manufactured on a single wafer. According to one embodiment, all oscillators are controlled and read using one control unit integrated on the same wafer.

According to one embodiment, there is provided at least one oscillator circuit loaded with a known reference impedance, such as a capacitor, and at least one, typically at least two, other oscillator circuit(s) to other component(s) to be measured. Preferably, all oscillators are fabricated on a single semiconductor wafer in order to minimize the variations between the responses of the oscillators. Thus, all differences in the measured responses (eg. offset frequency, sensitivity of frequency change as a function of control and non-linearity) can be expected to be due to different load impedances of the oscillators.

In addition to mass sensing using an FBAR-based sensor, the invention can be used in pressure, liquid or gas flow or acceleration sensing. For example, flow sensing can be implemented by coupling a plurality of FBAR sensors (2 or more) such that the liquid or gas can be diverted onto or into the vicinity of the sensors. As the temperature sensitivity of such sensors is extremely good, the magnitude of the flow can be detected. Previously, such implementations have been disclosed, for example, in www.memsic.com.cn/products/MXD2020.htm. The present measuring circuit provides for improved temperature sensitivity compared with known FBAR measurement solutions and thus allows smaller flows to be detected.

Example 1

Measurement Using a Mass Sensor as the Variable Impedance Component

This example illustrates the measurement of mass using a FBAR mass sensor. For simplicity, it is assumed that the influence of other factors than mass (e.g. temperature, viscosity, noise) are eliminated, standardized or compensated. The impedance analyser according to the invention is coupled to a FBAR mass sensor, whose surface is treated to be suitable to the desired purpose, for example, sensitive to a particular substance. The substance can increase the mass by adhering to the surface of the sensor or decrease the mass by disengaging molecules or particles from the surface of the sensor.

First, a reference measurement is carried out at an initial state of the sensor, which can be in e.g. vacuum or air or subjected to a suitable buffer/reference fluid. In the measurement, a desired control voltage range is swept over, the range typically covering the whole possible operational range of the circuit, i.e. at least the parallel resonance peaks of the sensor. For each voltage, the frequency of the circuit is recorded. If desired, a specific sub-range of the recently swept full range can be re-measured using a longer measurement time or smaller steps in the control voltage to increase the sensitivity or frequency resolution of the measurement. The measured reference data is stored for further analysis.

Next, the sensor is subjected to conditions where its mass is changed. This step may comprise addition of a substance of interest on the sensor by means of pipetting, for example, or immersion of the sensor to a substance of interest.

After that, the actual measurement is carried out in a similar fashion as the reference measurement.

If a (bio)active sensor surface is used, the sensor may be washed before the actual measurement to detach loose material from the sensor surface. Alternatively or in addition, the actual measurement can be performed in a buffer/reference liquid in order to standardize the ambient viscosity and, optionally, wash the sensor surface.

After the actual measurement, the data obtained in the measurements is analysed. That is, the change in frequency between the reference and actual measurements is determined at one or more points. If a plurality of points are used, the result may be averaged over the points. Correction of the results with respect to certain parameters, such as temperature may be carried at this point, if needed. Finally, the frequency change determined is converted to correspond to the mass change.

The invention claimed is:

1. A method for determining impedance of a variable impedance component, comprising
   tuning a tunable oscillator over a predefined tuning range, the tunable oscillator having the variable impedance component coupled as a load thereof,
   measuring the frequency response of the tunable oscillator as a function of said tuning, and
   analyzing the measured frequency response for determining the impedance of the variable impedance component,
   wherein the variable impedance component is a sensor or a resonator.

2. The method according to claim 1, wherein a sensor is used as the variable impedance component.

3. The method according to claim 2, wherein the sensor is a mass sensor.

4. The method according to claim 2, wherein the sensor is a bioactive mass sensor.

5. The method according to claim 1, wherein a resonator is used as the variable impedance component.

6. The method according to claim 5, wherein the resonator is a BAW resonator.

7. The method according to claim 5, wherein the resonator is an FBAR.

8. The method according to claim 1, wherein a resonator exhibiting at least two parallel resonance peaks is used as the variable impedance component.

9. The method according to claim 1, wherein the frequency response is measured using a frequency counter directly coupled to the tunable oscillator.

10. The method according to claim 1, wherein the step of determining the impedance comprises determining points where the derivative of the frequency response significantly changes.

11. The method according to claim 1, wherein the tunable oscillator is a voltage-controlled ring oscillator.

12. The method according to claim 11, wherein the tunable oscillator comprises a set of series-coupled semiconductor inverters.

13. The method according to claim 11, wherein the tunable oscillator comprises a set of series-coupled semiconductor inverters which are CMOS inverters.

14. The method according to claim 1, wherein the steps of tuning and measuring are carried out at least twice in different states of the variable impedance component and the step of analyzing comprises determining a difference in the respective resonating frequencies in at least one tuning point.

15. The method according to claim 1, wherein
- a resonator is used as the variable impedance component,
- an operation voltage is determined at which the frequency response of the tunable oscillator is locked to the vicinity of a resonance frequency of the resonator by tuning the tunable oscillator,
- a change of response of the variable impedance component at or in the vicinity of said operation voltage is determined between two different states of the variable impedance component.

16. The method according to claim 1, which comprises
- measuring the frequency response of the oscillator at least at two different points of operation and at least at two different temperatures,
- determining, using the at least two pairs of points obtained, a temperature compensation factor, and
- using the temperature compensation factor in said determination of impedance for performing a temperature compensation.

17. A system for determining the impedance of a variable impedance component, comprising
- a tunable oscillator,
- the variable impedance component coupled as a load of the tunable oscillator, wherein the variable impedance component is a sensor or a resonator,
- a tuning unit for tuning the tunable oscillator over a predefined tuning range, and
- a frequency counter coupled to the tunable oscillator for determining the frequency response of the tunable oscillator as a function of said tuning.

18. A system according to claim 17, wherein the tuning unit comprises
- a control unit capable of producing a digital control signal, and
- a D/A converter for producing an analogue control voltage for the tunable oscillator.

19. A system according to claim 17 or 18, wherein the tunable oscillator is manufactured as a monolithic structure on a semiconductor chip.

20. A system according to claim 19, wherein one or both of the tuning unit and the frequency counter is/are manufactured as a monolithic structure on the semiconductor chip.

21. A system according to claim 17, further comprising a plurality of tunable oscillators each loaded with different variable impedance components.

22. A system according to claim 21, further comprising a tunable oscillator loaded with a reference impedance.

23. A system according to claim 22, wherein the plurality of tunable oscillators and the tunable oscillator loaded with a reference impedance are manufactured on a single chip.

24. A system according to claim 21, wherein said plurality of tunable oscillators are manufactured on a single chip.

25. A microchip sensor device comprising in a monolithic structure
- a tunable ring oscillator, and
- an FBAR sensor coupled as a load of the tunable ring oscillator, and
- a terminal coupled to the tunable ring oscillator for measuring the oscillation frequency of the tunable ring oscillator.

26. A microchip sensor device according to claim 25, further comprising in the monolithic structure
- a frequency counter coupled to the terminal for measuring the oscillation frequency of the tunable ring oscillator.

27. A microchip sensor device according to claim 26, further comprising in the monolithic structure, a tuning unit for tuning the tunable ring oscillator.

* * * * *